United States Patent
Hussain et al.

(10) Patent No.: US 10,744,039 B2
(45) Date of Patent: *Aug. 18, 2020

(54) METHODS OF MAKING BIOACTIVE COLLAGEN WOUND CARE DRESSINGS

(71) Applicant: Ension, Inc., Pittsburgh, PA (US)

(72) Inventors: Ali Hussain, Cape Coral, FL (US); Patrick Cahalan, Cape Coral, FL (US); Linda Cahalan, Cape Coral, FL (US)

(73) Assignee: ENSION INC., Butler, PA (US)

( * ) Notice: Subject to any disclaimer, the term of this patent is extended or adjusted under 35 U.S.C. 154(b) by 288 days.

This patent is subject to a terminal disclaimer.

(21) Appl. No.: 15/790,851

(22) Filed: Oct. 23, 2017

(65) Prior Publication Data

US 2018/0064580 A1 Mar. 8, 2018

Related U.S. Application Data

(63) Continuation-in-part of application No. 14/041,372, filed on Sep. 30, 2013, now Pat. No. 9,796,769.

(60) Provisional application No. 61/788,720, filed on Mar. 15, 2013, provisional application No. 61/706,930, filed on Sep. 28, 2012.

(51) Int. Cl.

| | | |
|---|---|---|
| *A61F 13/00* | (2006.01) | |
| *C07K 14/78* | (2006.01) | |
| *A61L 15/32* | (2006.01) | |
| *A61L 15/42* | (2006.01) | |
| *A61L 27/20* | (2006.01) | |
| *B32B 5/10* | (2006.01) | |
| *A61K 38/39* | (2006.01) | |
| *A61L 27/24* | (2006.01) | |
| *A61L 31/14* | (2006.01) | |
| *A61L 31/04* | (2006.01) | |

(52) U.S. Cl.
CPC .. *A61F 13/00012* (2013.01); *A61F 13/00029* (2013.01); *A61K 38/39* (2013.01); *A61L 15/325* (2013.01); *A61L 15/425* (2013.01); *A61L 27/20* (2013.01); *A61L 27/24* (2013.01); *A61L 31/044* (2013.01); *A61L 31/146* (2013.01); *B32B 5/10* (2013.01); *C07K 14/78* (2013.01); *A61F 2013/00604* (2013.01); *B32B 2250/20* (2013.01)

(58) Field of Classification Search
CPC .......... A61F 13/00012; A61F 13/00029; A61F 2013/00604; A61K 38/39; A61L 15/325; A61L 15/425; A61L 27/20; A61L 27/24; A61L 31/044; A61L 31/146; B32B 2250/20; B32B 5/10; C07K 14/78
See application file for complete search history.

(56) References Cited

U.S. PATENT DOCUMENTS

| | | | |
|---|---|---|---|
| 4,840,626 | A | 6/1989 | Linsky et al. |
| 6,117,979 | A | 9/2000 | Hendriks et al. |
| 7,172,765 | B2 | 2/2007 | Chu et al. |
| 7,749,204 | B2 | 7/2010 | Dhanaraj et al. |
| 7,815,923 | B2 | 10/2010 | Johnson et al. |
| 9,796,769 | B2 * | 10/2017 | Hussain ................ C07K 14/78 |

FOREIGN PATENT DOCUMENTS

| | | |
|---|---|---|
| EP | 0 262 890 | 4/1988 |
| EP | 0 372 969 | 6/1990 |
| EP | 1 707 260 | 4/2006 |
| WO | 2004043351 | 5/2004 |

OTHER PUBLICATIONS

J. Höerl, L. Fischer2, A. Schachtrupp3, JLaparotomy Closure and Incisional Hernia Prevention—What are the Surgical Requirements? Zentralblatt Fur Chirurgie, vol. 136, No. 1 pp. 42-49 2011.
Teruo Miyata, Masayasu Fususe, Yoshihisa Yamane, Yasuharu Noishiki, A Biodegradable Antiadhesion Collagen Membrane with Slow Release Heparin, Trans Am Soc Artif Intern Organs, pp. 687-691, Fol. XXXIV, 1988.
Utah.edu "Lab 3—Introduction to Sutures", Univ. of Utah, <URL:http://www.bioen.utah.edu/faculty/pat/Courses/biomaterials/Lab3.d- oc>, archived online Dec. 18, 2005, 5 pages.
Yang, Chunrong "Enhanced physicochemical properties of collagen by using EDC/NHS-crosslinking" Bull. Mat. Sci., 35(5), Oct. 23, 2012, pp. 913-918.
Bowes, J.H and Cater, C.W. "The Interaction of Aldehydes with Collagen" Biochimica et Biophysica Acta (BBA)—Protein Structure, Oct. 1968, 2(21), 341-352 (abstract only).
Lodish, H; Berk, A; and Zipursky, SL, Molecular Cell Biology, 4th ed., W.H.Freeman (ed.), 2000, .sctn.22.3: "Collagen: The Fibrous Protein Matrix", 6 pages.
Nam, Kwangwoo; Kimura, Tsuyoshi; Funamoto, Seiichi;Kishida, Akio "Preparation of a collagen/polymer hybrid gel designed for tissue membranes. Part I: Controlling the polymer—collagen crosslinking process using an ethanol/water co-solvent" Acta Biomaterialia, Feb. 2010 (pub online Jun. 14, 2009), 6(2), 403-408.

(Continued)

*Primary Examiner* — Aaron J Kosar
(74) *Attorney, Agent, or Firm* — Blynn L. Shideler; Krisanne Shideler; BLK Law Group

(57) ABSTRACT

A method of preparing a crosslinked, collagen-based wound care dressing is provided, comprising: (a) immersing a sample of fibrous and/or non-fibrous collagen in a buffered acidic, aqueous solution comprising an alcohol; (b) contacting the collagen in solution with a catalytic component comprising 1-ethyl-3-[3-dimethylaminopropyl]carbodiimide hydrochloride for a time at least sufficient to effect reaction between amino and carboxyl groups present on the collagen and to yield crosslinked collagen that is resistant to pronase degradation; and (c) drying the crosslinked collagen to yield a porous, crosslinked collagen article wherein the porous, crosslinked collagen article demonstrates a pore size of 10-500 microns. Also provided are bioactive collagen medical scaffolds for hernia repair prosthetics and surgical incision closure members, prepared using the method above.

20 Claims, 3 Drawing Sheets

(56) References Cited

OTHER PUBLICATIONS

Nam, Kwangwoo; Kimura, Tsuyoshi; Kishida, Akio "Controlling Coupling Reaction of EDC and NHS for Preparation of Collagen Gels Using Ethanol/Water Co-Solvents" Macromol. Biosci. 2008, 8, 32-37.

Raymond Zeeman, Pieter J. Dijkstra, Pauline B. van Wachem, Marja J.A. van Luyn, Marc Hendriks, Patrick T. Cahalan, Jan Feijen "Successive epoxy and carbodiimide cross-linking of dermal sheep collagen" Biomaterials, 1999, 20, pp. 921-931.

Cheville, Norman F. "The Extracellular Matrix", Ultrastructural Pathology: The Comparative Cellular Basis of Disease, 2nd ed., 2009 Ch.12, pp. 295-316.

M.J.B. Wissink, R. Beernink, J.S. Pieper, A.A. Poot, G.H.M. Engbers, T. Beugeling, W.G. van Aken, J. Feijen "Immobilization of heparin to EDC/NHS-crosslinked collagen. Characterization and in vitro evaluation" Biomaterials, 2000, 22, pp. 151-163.

* cited by examiner

FIG. 4A
PRIOR ART
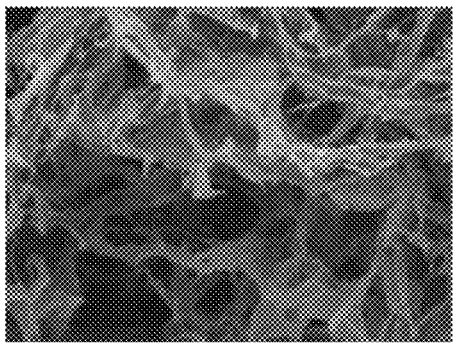
FIG. 4B
PRIOR ART
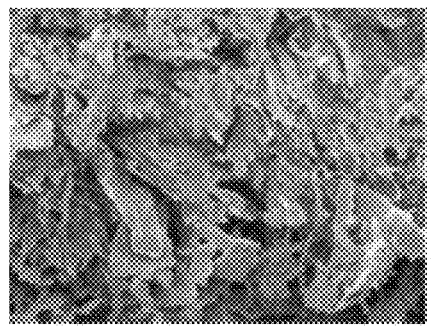
FIG. 5A
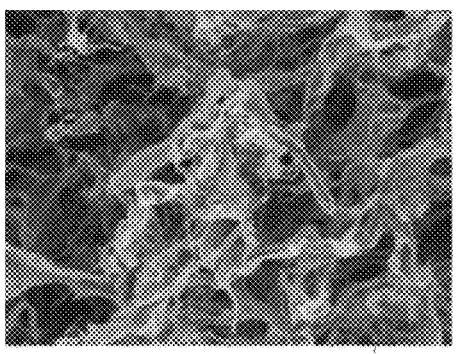
226
FIG. 5B  226
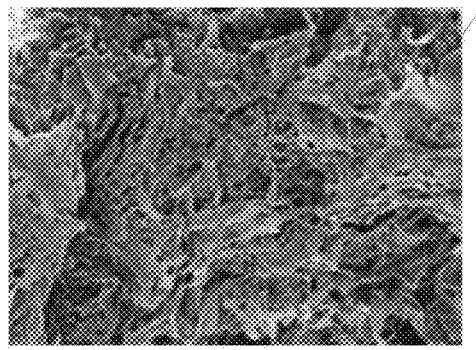
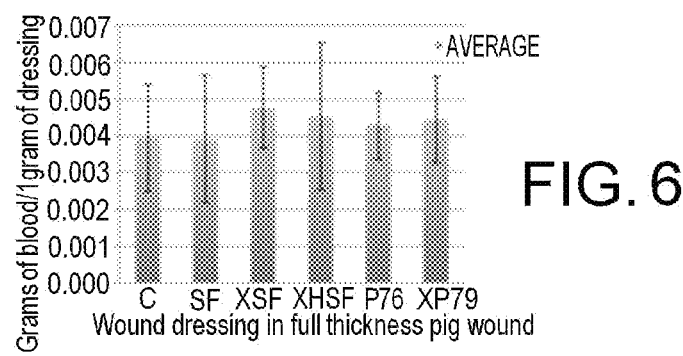
FIG. 6

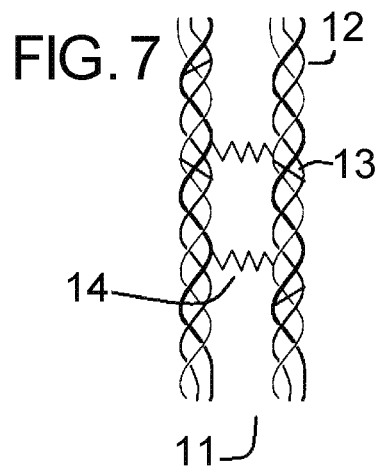
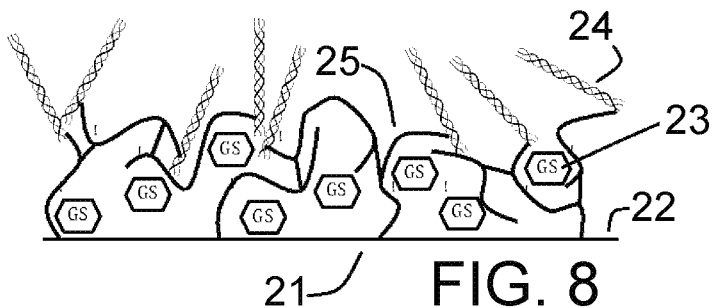
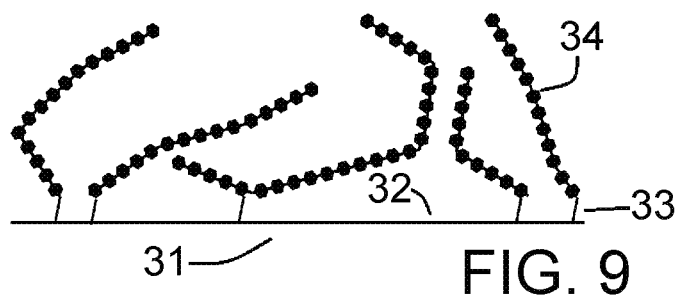
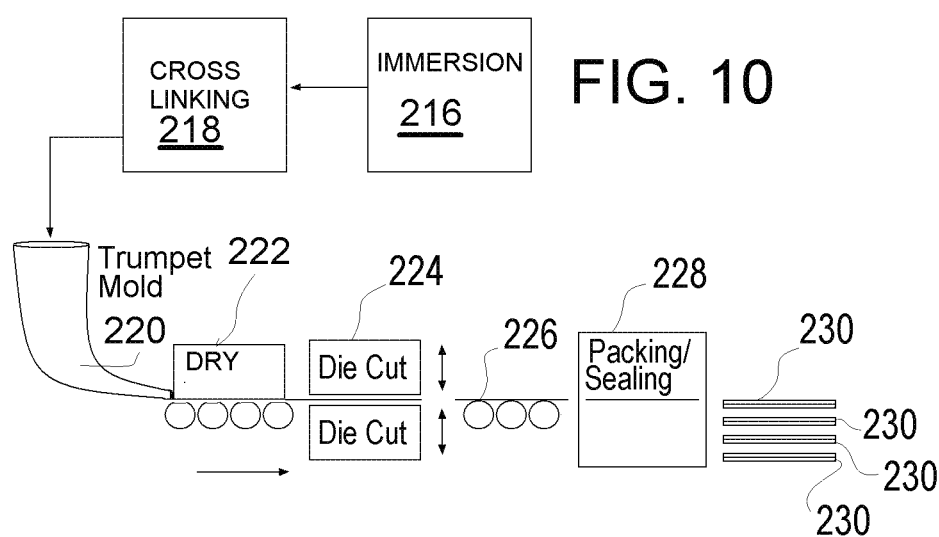

METHODS OF MAKING BIOACTIVE COLLAGEN WOUND CARE DRESSINGS

RELATED APPLICATIONS

This application is a continuation in part of U.S. patent application Ser. No. 14/041,372 filed Sep. 30, 2013, published Apr. 3, 2014 as publication 2014-0093912 and issued Oct. 24, 2017 as U.S. Pat. No. 9,796,769, which patent and publication are incorporated herein by reference.

U.S. patent application Ser. No. 14/041,372 claims priority to U.S. Provisional Patent Application Ser. No. 61/706,930 filed Sep. 28, 2012, entitled "Bioactive Collagen Medical Scaffolds for Wound Care Dressings, Hernia Repair Prosthetics, and Surgical Incision Closure Members and Methods of Making Same".

U.S. patent application Ser. No. 14/041,372 claims priority to U.S. Provisional Patent Application Ser. No. 61/788,720 filed Mar. 15, 2013, entitled "Bioactive Collagen Medical Scaffolds for Wound Care Dressings, Hernia Repair Prosthetics, and Surgical Incision Closure Members and Methods of Making Same".

STATEMENT REGARDING FEDERALLY SPONSORED RESEARCH OR DEVELOPMENT

This invention was developed, in part, with support by the United States Government under agreement number W81XWH-11-C-0472 with the Department of Defense (DOD). The United States Government may have certain rights in the invention.

BACKGROUND OF THE INVENTION

Field of the Invention

The present invention relates to bioactive collagen medical scaffolds for wound care dressings, hernia repair prosthetics, and surgical incision closure members and methods of making these articles.

Wound Care Dressing Background

Wound healing is a complex and dynamic process with the wound environment changing with the changing health status of the individual. The knowledge of the physiology of the normal wound healing trajectory through the phases of hemostasis, inflammation, granulation and maturation provides a framework for an understanding of the basic principles of wound healing.

Collagen is a natural biomaterial that has unique properties and has been used for health care since the ancient Egyptian civilization. Collagen is the most abundant protein found in the body and there are 13 different types of collagen. Chains of amino acids make up collagen and form collagen molecules which in turn, from fibrils. These fibrils produce fibers. Bundled fibers lead to body tissue formation. Distribution and orientation of collagen reflects the function of the tissue in which it is found. For example, it is collagen that transmits tension in tendon, lends structural support in skin and bone and limits expansion in arteries.

Collagen plays an integral part during each phase of wound healing and is an excellent hemostatic agent. It absorbs 40-60 times its weight in fluid. When applied to a wound, collagen initially acts as a hemostatic agent and continued application seems to aid and hasten the body's own repair mechanisms.

There are a number of different collagen based wound care dressings currently available, which employ a variety of carriers/combining agents such as gels, pastes, polymers, oxidized regenerated cellulose (ORC), and ethylene diamine tetraacetic acid (EDTA). The collagen within these products tends to be derived from bovine, porcine, equine, or avian sources, which is purified in order to render it non-antigenic. The collagen in a given collagen dressing can vary in concentration and type. Certain collagen dressings are comprised of Type I (native) collagen; whereas, other collagen dressings contain denatured collagen as well. A given collagen dressing may contain ingredients, such as alginates and cellulose derivatives that can enhance absorbency, flexibility, and comfort, and help maintain a moist wound environment. Existing collagen dressings have a variety of pore sizes and surface areas, as well. All of these attributes are meant to enhance the wound management aspects of the dressings. Many collagen dressings contain an antimicrobial agent to control pathogens within the wound. Existing collagen dressings typically require a secondary dressing.

Research has suggested that some collagen-based dressings produce a significant increase in the fibroblast production; have a hydrophilic property that may be important in encouraging fibroblast permeation; enhance the deposition of oriented, organized collagen fibers by attracting fibroblasts and causing a directed migration of cells; aid in the uptake and bioavailability of fibronectin; help preserve leukocytes, macrophages, fibroblasts, and epithelial cells; and assist in the maintenance of the chemical and thermostatic microenvironment of the wound.

There remains a need to provide improved collagen based wound care dressings that are non-antigenic that further augment the natural healing process and degrade within the wound in a controlled manner without producing byproducts that generate an immune response.

Hernia Background

Hernias have plagued humans throughout recorded history, and descriptions of hernia reduction date back to Hammurabi of Babylon and early Egyptian writings. A hernia is usually a protrusion or sac formed by the lining of the abdominal cavity, the peritoneum. The hernia sac protrudes through the hernia defect, i.e. a hole or weak area, in the fascia. The fascia is the strong layer of the abdominal wall that surrounds the muscle. There are various types of hernias including ventral hernias, incisional hernias inguinal hernias, hiatal hernias, femoral hernias, diaphragmatic hernias, diverticular hernias, barth hernias, epigastric hernias, interstitial hernias, sciatic hernias and umbilical hernias, defined largely by the location of the hernia defect. This is merely an illustrative and not a comprehensive listing of hernia classifications and the above listing is not mutually exclusive, for example an incisional hernia through a prior laparotomy incision may be referenced as a ventral hernia.

Surgery is essentially the only treatment that can permanently fix a hernia. Original hernia surgery utilized the patients existing tissue to repair the defect and this technique is now known as "pure tissue" repair of a hernia defect. Dr. Bassini has been noted as an early pioneer in successful pure tissue repair of hernias when in 1888 he reported a reduction in the recurrence rate of pure tissue hernia repair to about 10% (from a conservative estimated 30-40% rate earlier) with his procedure that combined an understanding of anatomy with an application of surgical thinking and surgical technique. This 10% recurrence rate is quite impressive when noted that it was achieved at a period without antibiotics, primitive anesthesia and at a time when patients often suffered with their hernia until they reached a giant size before submitting to surgery. For well over a century, Bassini's pure tissue repair procedures, with several modifications (e.g. Halsted, McVay, Tanner, Shouldice . . . ) have helped preserve useful life in hundreds of thousands cases.

Hernia repair prosthetics have been developed, also called hernia repair patches, hernia repair meshes and hernia repair fabrics, for use in what is commonly known as a tension free repair of a hernia defect. The hernia repair prosthetic generally plugs and/or bridges the gap forming the defect and the patient's tissue is not "stretched" over the defect, thus allowing the tissue to remain "tension free". The tension-free repair is invariably linked to Dr. Lichtenstein whose work and progress over two decades culminated in what is known as the tension free Lichtenstein repair. The precise amount of reoccurrence varies with the type of hernia and the associated tension free procedure utilized, but in essentially all cases the "tension free" prosthetic repair substantially reduces reoccurrence of hernias over the pure tissue repair, and provides a minimized recovery period. Further, tension free prosthetic hernia repair further yielded a decrease in surgery time and in post-operative patient pain and thus has become the most popular repair for hernia defects.

Numerous surgically implantable hernia repair prosthetics have been proposed. Hernia repair mesh prosthesis formed of synthetic materials such as polypropylene (PP), polyester (PET), and polytetraflouroethylene (PTFE), and combinations thereof are some of the most common synthetic based hernia repair prosthetics. Hernia repair mesh prosthesis formed of non-synthetic or biological materials have also been proposed, with some biological prostheses designed for permanent placement within a patient's body space and others designed for partial or complete absorption into the patient's body over time after the hernia defect has been fully repaired. The general premise of most biologic hernia repair prosthetics is to create a scaffold to allow cellular in-growth and tissue remodeling.

There has been some question regarding whether such products are strong enough to bridge large defects in the long term, thus limiting their use for routine abdominal wall hernia repair. Biological hernia repair prosthetic material is derived from human and non-human (porcine, bovine and even avian) sources. Material from non-human sources may also undergo cross-linking. In general, as cross-linking density increases, so does fibroblast encapsulation and implant resistance to enzymatic degradation; however, the rate of cellular infiltration decreases. It has been noted that the optimum cross-linking pattern and density to balance graft strength and durability with cellular in-growth and remodeling remain uncertain.

U.S. Pat. No. 7,749,204, incorporated herein by reference, discloses a reinforced absorbable multilayered fabric for use in tissue repair and regeneration described as directed to a method of using a multilayered fabric comprising a first absorbable nonwoven fabric and a second absorbable woven or knitted fabric in tissue repair and regeneration. The patent adds that additionally, the reinforced absorbable multilayered fabric may contain bioactive agents to aid in the repair or regeneration of tissue. Examples of bioactive agents include cell attachment mediators, such as peptide-containing variations of the "RGD" integrin binding sequence known to affect cellular attachment, biologically active ligands, and substances that enhance or exclude particular varieties of cellular or tissue ingrowth.

U.S. Pat. No. 7,815,923, incorporated herein by reference, discloses an implantable graft material that is suitable for implantation within a patient including isolated tissue material remodeled in a body cavity. The patent states that in "addition to being cross linked, the ECM material can be treated (e.g., brought into contact, impregnated, coated, etc.) with one or more desirable compositions, such as anticoagulants (e.g., heparin), growth factors, other desirable property modifiers, and the like to modify the tissue properties."

Although these medical advances in the field of hernia repair prosthetics are acknowledged for their usefulness and success in reducing the incidence of reoccurrence of the hernia, there remains a need for greater improved collagen based hernia repair prosthetics that further augment the natural healing process while providing sufficient strength and flexibility for the intended application while providing a solution that is cost effective to manufacture and implement.

Incisional Closure

A laparotomy, also called a celiotomy, is a surgical procedure involving a large incision through the abdominal wall to gain access into the abdominal cavity. Several hundred thousand laparotomy incisions are created each year and the failure rate for closure of these abdominal wounds is estimated between 10-15% (sometimes estimated as high as 20%), creating a large problem of incisional hernia.

An incisional hernia is a type of hernia caused by an incompletely-healed surgical wound. Since median incisions in the abdomen are frequent for abdominal exploratory surgery, ventral incisional hernias are often termed ventral hernias. These can be among the most frustrating and difficult hernias to treat. In the light of an incisional hernia incidence of between 10 and 20% that remains constantly high in spite of modifications of suture materials and suture techniques, intensified scientific efforts aiming at incisional hernia prevention are warranted. It has been noted that currently there is a lack of empirical data and a lack of a clear current consensus concerning the ideal material and technique to close laparotomies. Experimental studies have demonstrated the negative effects of conventional laparotomy closure on the abdominal where histology and laser-fluorescence angiography revealed the weakening of abdominal wall structures and abdominal wall perfusion after directly suturing the incisional edges. Additionally, it has been observed that inadequate suture-tension may have an influence on collagen quantity and quality in the healing incision. Measures to prevent incisional hernia formation, which has been identified as the post-operative complication in surgery most frequently leading to re-operation, require intensified attention. In addressing this problem it has been suggested that "success will only be achieved if the development of unconventional closure techniques is encouraged and the beaten path of suturing the incisional edges is discarded." See Zentralblatt Fur Chirurgie, Volume 136, No. 1 pp 42-49 2011.

The use of collagen barrier for surgical incisions to prevent adhesions is known where there is a placement of a physical barrier between the surgical site and the surrounding tissue where adhesions are most commonly encountered. For example, in an article entitled "Heparin Releasing Antiadhesive Membranes" by Y. Noishiki and T. Miyata published in Jinko Zoki, 14(2), p. 788-79 1 (1985), a collagen membrane (special treated human amnion) having protamine cross-linked into the collagen network was immersed in 1% heparin solution so the heparin was ionically bound to the protamine which had been cross-linked in the collagen. The resultant heparinized collagen membrane was stitched into place covering a wound on the serosal membrane of the large intestines of dogs. The animals were examined after 3 days, 60 days, 173 days and 687 days. No signs of adhesions were found. These collagen membranes were not biodegradable, since much of the material remained even after 687 days. The heparin was released slowly and steadily, so that 76% of the heparin originally present in the membrane was released over a period of three months.

U.S. Pat. No. 7,172,765 notes that various materials, including cross-linked collagen webs, have also been used to form physical barriers in an attempt to prevent adhesions, including silicone elastomers, gelatin films and knit fabrics of oxidized regenerated cellulose (hereinafter ORC). In some cases This patent notes that it is suggested that heparin, heparinoid, or hexuronyl hexosaminogly can be incorporated into the matrix of an ORC fabric or other matrices of hyaluronic acid, cross-linked and uncross-linked collagen webs, synthetic resorbable polymers, gelatin films, absorbable gel films, oxidized cellulose fabrics and films which are fabricated into a form that is said to be "drapable, conformable and adherent to body organs" and substantially absorbable within 30 days. This patent references U.S. Pat. No. 4,840,626, EPA Publication No. 0 262 890 and EPA Publication No. 0 372 969 as examples of this point. However, this patent suggests it is difficult to precisely control the degradation rate of many of these materials and scar tissue can result from use of many of the materials.

It would be desirable to provide a biologic structure to reinforce a surgical incision to promote healing and reduce the occurrence of post-operative complications such as incisional hernias.

BRIEF DESCRIPTION OF THE DRAWINGS

FIG. 4*a* is an SEM image of a sample of prior art fibrous collagen that has not undergone the process of the present invention.

FIG. 4*b* is an SEM image of the sample of the prior art fibrous collagen from FIG. 4*a*, after administration to a wound as a dressing.

FIG. 5*a* is an SEM image of a sample of fibrous collagen made according to the process of the present invention.

FIG. 5*b* is an SEM image of the sample of fibrous collagen from FIG. 5*a*, after administration to a wound as a dressing.

FIG. 6 is a graphical comparison of the blood absorption per gram of wound dressing per second of various wound dressings prepared according to the process of the present invention versus several comparative controls.

FIG. 7 is a schematic illustration of a crosslinked collagen molecule prepared in accordance with the present invention.

FIG. 8 is a schematic illustration of a medical device comprising a crosslinked collagen molecule surface treated with a hydrogel and containing biomolecules prepared in accordance with the present invention.

FIG. 9 is a schematic illustration of a medical device comprising a crosslinked collagen molecule containing biomolecules prepared in accordance with the present invention.

FIG. 10 is a schematic representation of the process of making bioactive collagen medical scaffolds of the present invention.

SUMMARY OF THE INVENTION

The present invention provides bioactive collagen medical scaffolds such as wound care dressings, hernia repair prosthetics, and surgical incision closure members. The invention also provides methods of making these articles, comprising: (a) immersing a sample of fibrous and/or non-fibrous collagen in a buffered acidic, aqueous solution comprising an alcohol; (b) contacting the collagen in solution with a catalytic component comprising 1-ethyl-3-[3-dimethylaminopropyl]carbodiimide hydrochloride for a time at least sufficient to effect reaction between amino and carboxyl groups present on the collagen and to yield crosslinked collagen that is resistant to pronase degradation when subjected to PRONASE DEGRADATION TEST for at least five hours; and (c) drying the crosslinked collagen to yield a porous, crosslinked collagen article wherein the porous, crosslinked collagen article demonstrates a pore size of 10-500 microns.

DETAILED DESCRIPTION

Figure 1:
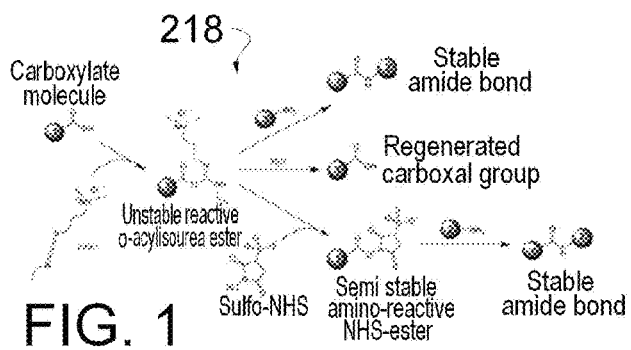
FIG. 1 illustrates possible reaction schemes that may occur in the cross linking step of the process of the present invention.

FIG. 10 is a schematic representation of a scalable process of making bioactive collagen medical scaffolds 226 of the present invention with the scaffolds 226 useful as wound care dressings, hernia repair prosthetics, and surgical incision closure members. The process includes an immersion step 216 followed by a cross linking step 218, each of which will be described in greater detail below at the heart of the process of the present invention. FIG. 1 illustrates possible reaction schemes that may occur in the cross linking step 218 of the process of the present invention. For manufacturing purposes following cross-linking, or simultaneous therewith, the medical scaffold forming material is forwarded to a molding step, such as a trumpet mold 220, then to a drying station 222 and to a shaping or cutting station 224 to form the individual medical scaffolds 226 of the desired shape. The medical scaffolds 226, which may be wound care dressings, hernia repair prosthetics, and surgical incision closure members or other medical devices, are then packaged/sealed and sterilized in a conventional fashion at 228 to form packaged units 230 of the medical scaffolds 226. The trumpet mold 220, drying 222 and die cutting 224 could also be replaced with a series individual molds shaped in the final product configuration with a drying station 222, however the trumpet mold 220 and die cutting 224 represents a more easily modified process to changes in the final product dimensions.

Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("$M_n$") or weight average molecular weight ("$M_w$")), and others in the following portion of the specification may be read as if prefaced by the word "about" even though the term "about" may not expressly appear with the value, amount or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

Plural referents as used herein encompass singular and vice versa. For example, while the invention has been described in terms of "a" biomolecule, a plurality, including a mixture of such molecules can be used.

Any numeric references to amounts, unless otherwise specified, are "by weight".

As used herein, the term "polymer" is meant to refer to prepolymers, oligomers and both homopolymers and copolymers; the prefix "poly" refers to two or more.

As used herein, "formed from" denotes open, e.g., "comprising," claim language. As such, it is intended that a composition "formed from" a list of recited components be a composition comprising at least these recited components, and can further comprise other non-recited components during the composition's formation.

The collagen used in the process of the present invention may be fibrous or non-fibrous, or a mixture thereof. The term "collagen" refers to a group of naturally occurring proteins found in animals, especially in the flesh and connective tissues of vertebrates. It is the main component of connective tissue, and is the most abundant protein in mammals, making up about 25% to 35% of the protein content in a body. The collagen used in the process of the present invention may be derived from human, bovine, porcine, avian, equine or other tissue.

A collagen molecule is in the form of a triple helix, which generally consists of two identical chains and an additional chain that differs slightly in its chemical composition. The most common motifs in the amino acid sequence of collagen are Glycine-Proline-X and Glycine-X-Hydroxyproline, where X is any amino acid other than glycine, proline or hydroxyproline. Free reactive functional groups including carboxyl and amino groups occur along the collagen chain. Each collagen molecule is approximately 300 nm long and 1.5 nm in diameter, and is made up of three polypeptide strands as mentioned above, each possessing the conformation of a left-handed helix. These three left-handed helices are twisted together into a right-handed "coiled coil", a triple helix or "super helix", stabilized by numerous hydrogen bonds. In fibrous collagens, each triple-helix associates into a right-handed super-super-coil referred to as a collagen microfibril.

In certain embodiments of the present invention, depending on the source of the collagen, if the sample is of fibrous collagen the sample may be broken down and "reconstituted" in order to purify the sample. For example, a sample of fibrous collagen may be soaked in an aqueous solution of acetic acid for a time sufficient to separate the fibrous strands. The separated strands may then be rinsed and recombined into fibrous strands.

In certain embodiments of the present invention, the collagen may comprise an extracellular matrix (ECM). The ECM is the extracellular part of human or animal tissue that usually provides structural support to the animal cells in addition to performing various other important functions. The ECM comprises an interlocking mesh of glucosaminoglycans (GAGs) and fibrous proteins including collagen, and is the defining feature of connective tissue in animals. A typical extracellular matrix includes an interstitial matrix and a basement membrane. In the body, interstitial matrix is present between various animal cells (i. e., in the intercellular spaces). Gels of polysaccharides and fibrous proteins fill the interstitial space and act as a compression buffer against the stress placed on the ECM in the body. Basement membranes are sheet-like depositions of ECM on which various epithelial cells rest in the body. Human based ECM products are available from LifeCell Corporation under the ALLODERM® brand, Musculoskeletal Tissue Foundation under the FLEXHD® brand, Davol, Inc. under the ALLOMAX® brand. Non-human based ECM products are also commercially available from a variety of sources.

In the "Immersion" step (a) of the process of the present invention shown at 216 of FIG. 10, the collagen is immersed in a buffered acidic, aqueous solution comprising an alcohol. Suitable alcohols include $C_1$ to $C_6$ alcohols such as ethanol. The solution may be buffered with a non-carboxylic acid buffer such as 2-morpholinoethane sulfonic acid (MES) to a pH ranging from 4.7 to 6.0. In a typical embodiment of the invention, the collagen is immersed in an aqueous solution with a pH of 5, comprising a mixture of 40 percent by volume ethanol and 60 percent by volume 50 mM MES Immersion typically takes place with agitation at ambient temperature or less, for a time sufficient to hydrate the collagen sample; 15 to 30 minutes is typically sufficient. Temperatures may be lower or higher but caution must be taken to prevent degradation of the collagen, thus ambient temperatures or lower are preferred.

After the immersion step (a) 216, the collagen may be drained and/or rinsed with a fresh buffer solution such as one having the composition used above.

Figure 2A:
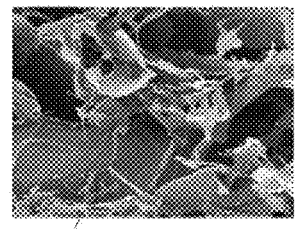
FIG. 2*a* is a scanning electron micrograph (SEM) image of a sample of a fibrous bovine collagen after cross linking step of the process of the present invention.
Figure 2B:
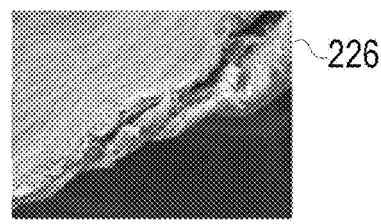
FIG. 2*b* is a scanning electron micrograph (SEM) image of a sample of a fibrous bovine collagen after the freeze drying step of the process of the present invention.

In certain embodiments of the present invention, prior to the "Cross Linking" step (b) shown at 218 in FIG. 10, a portion (less than 100 percent, such as 10 to 50 percent or 10 to 25 percent) of free amino functional groups on the collagen may be reacted with a blocking agent such as a $C_1$ to $C_6$ or higher aldehyde, in a buffer solution such as one having the composition used above. This reaction blocks a portion of the amino groups and allows one to tailor the subsequent crosslinking reaction of the collagen with respect to crosslink density and sites. It may be possible to deblock the blocked amino groups after crosslinking, making these functional groups available for subsequent reaction with, for example, biomolecules. Suitable aldehydes include formaldehyde, ethanal, propanal, n-butanal, and the like. FIG. 2a is a scanning electron micrograph (SEM) image of a sample of a fibrous bovine collagen 219 after the cross linking step 218 of the process of the present invention and before drying. FIG. 2b is a scanning electron micrograph (SEM) image of a sample of a fibrous bovine collagen 226 after the freeze drying step of the process of the present invention, discussed below.

In an additional or alternative embodiment of the present invention, prior to step (b), at least a portion of reactive functional groups on the collagen may be reacted with one or more $C_2$ to $C_{18}$ carboxylic acids having amino and/or hydroxyl functional groups. These carboxylic acids serve as functional "spacer linkages" on the collagen strands. The reactions may be conducted via typical esterification or amidation reactions. A single carboxylic acid molecule may be reacted with functional groups on the collagen, or a plurality of carboxylic acids (two or more) may be polymerized to make longer spacer linkages in a chain branching out from the collagen surface. The addition of spacer linkages on the collagen allows for greater mechanical flexibility of the final crosslinked collagen due to voids between the individual strands of collagen. Suitable carboxylic acids include hydroxyl functional acids, for example, alpha-hydroxy acids such as ascorbic acid, and amino acids.

In cross linking step (b) of the method of the present invention shown as 218 in FIG. 10, the collagen is contacted in solution with a catalytic component. The catalytic component comprises 1-ethyl-3-[3-dimethylaminopropyl]carbodiimide hydrochloride (EDC), present in at least catalytic amounts. Contact occurs for a time at least sufficient to effect reaction between amino and carboxyl groups present on the collagen, and to yield a crosslinked collagen. FIG. 1 illustrates a reaction scheme between carboxyl functionality on a collagen molecule 1 and EDC, forming a reactive o-acylisourea ester intermediate. This reaction is reversible; the intermediate may revert back to the carboxyl functional collagen by reaction with water in the aqueous medium. In addition, the intermediate reacts with a collagen molecule 2 to form a chemically stable crosslink between the two collagen molecules 1 and 2 via an amide bond.

Crosslink density may be measured using Fourier Transform Infrared analysis (FTIR) and is reported as the inverse of the ratio of the absorption peak of a sample at 1553 $cm^{-1}$ to the absorption peak at 1456 $cm^{-1}$. The peak at 1553 $cm^{-1}$ corresponds to the quantity of $NH_2$ which is converted to NH during condensation crosslinking reactions. A decrease in the 1553 $cm^{-1}$ intensity is proportional to an increase in the number of crosslinks within the collagen molecules. The peak at 1456 $cm^{-1}$ corresponds to —$CH_2$ deformation and —$CH_3$ asymmetric deformation.

Reaction between amino and carboxyl groups present on the collagen to form amide crosslinks may take place between any amino and carboxyl groups present on the collagen, such as directly between free amino and carboxyl groups originally present on the collagen and which are integral to the amino acids that form the collagen, or between amino and carboxyl groups present on the spacer linkages, or combinations thereof. The reaction is catalyzed by the catalytic component, which may further comprise N-hydroxysulfosuccinimide (NHS).

As shown in FIG. 1, NHS may react with carboxyl groups on a collagen molecule 1 to form an intermediate amine-reactive NHS ester, which is semi-stable. This intermediate then reacts with amino groups on a collagen molecule 2 to form a chemically stable crosslink between the two collagen molecules 1 and 2 via an amide bond.

Crosslinking reactions between functional groups may be intrahelic, interhelic, intrafibril, and/or interfibril. For example, reactions may occur within the interior of a triple helix, between strands of separate helices, and within or between fibrils.

Typically contact between the collagen and the catalytic component continues for at least one hour, such as at least 2 hours, or at least 4 hours. After about twelve hours there may be too few free functional groups to react. The reaction is typically conducted at or below ambient temperature to preserve the chemical integrity of the collagen.

In an exemplary embodiment of the present invention, 14 mM EDC and 8 mM NHS solutions are added to a buffer solution at 0.27 percent by weight and 0.092 percent by weight, respectively, and the crosslinking reaction allowed to progress at ambient temperature for 4 hours with agitation. FIG. 2a illustrates an SEM image of a cross-section of crosslinked, fibrous bovine collagen after step (b).

In certain embodiments of the present invention, immediately prior to, simultaneously with, or immediately after step (b), at least a portion of reactive functional groups on the collagen may be reacted with one or more biomolecules having carboxylic acid, amino and/or hydroxyl functional groups, thereby surface-treating the collagen. Biomolecules such as growth factors including fibroblast growth factor or vascular endothelial growth factor (VEGF), a glycosaminoglycan (GAG) such as heparin, an antibacterial agent, an antimicrobial agent, an anticoagulant, an antithrombotic agent, a platelet agent, an anti-inflammatory compound, an enzyme, a bioreaction catalyst, a hormone, a drug, a vitamin, an antibody, an antigen, a nucleic acid, a dye, a DNA segment, an RNA segment, a protein, a peptide, and the like, may be chemically (covalently) bonded to the collagen in this way.

In an exemplary scenario, 1 mg/ml dehydrated heparin may be added to a 0.5 M NaCl solution and the pH adjusted to 4.0. To this solution, 0.05 mg/ml sodium cyanoborohydride (NaCNBH) may be added and the resulting solution added to the buffered, crosslinked collagen. Reaction is permitted to proceed at ambient temperature under agitation for eighteen hours.

After step (b), the collagen may be drained and/or rinsed one or more times with a fresh buffer solution such as one having the composition used above, deionized water, an aqueous alcohol solution such as 40 percent by volume solution of ethanol, and/or saline.

In the drying step (c) of the method of the present invention shown as 222 of FIG. 10, the crosslinked collagen is dried. The collagen may be rotary dried, spray dried, thermally or radiantly dried, or freeze dried, which is preferred.

In an illustrative freeze-drying (lyophilization) process, slurries of the crosslinked collagen are introduced into a freeze dryer. In a first cycle, the temperature is decreased steadily from ambient temperature to −40° C. over 65 minutes. The temperature is then held constant at −40° C. for two hours in the second cycle. The third cycle includes rapid temperature increase to 0° C. under a vacuum of 100 mT, followed by a constant temperature hold under vacuum at 0° C. for 17 hours. A secondary drying takes place in a fourth cycle, which includes rapid warming to 5° C., a constant temperature hold at 5° C. for one hour, and a steady return to ambient temperature over another hour prior to releasing the vacuum. FIG. 2b is a scanning electron micrograph (SEM) image of a sample of a fibrous bovine collagen 226 after freeze drying in step (c).

Prior to step (c) of the method of the invention, the crosslinked collagen may be introduced as a slurry into a mold of a desired shape or onto a pan that will allow for cutting or stamping into a final desired shape. A trumpet mold 220 shown in FIG. 10 may be used to implement the present invention is a scalable manner. The mold can continuously mold into a sheet that moves through the drying unit 222 prior to cutting to desired shape at 224 and into units 226 that are packaged at 228 into sealed sterilized units 230.

In the above described processing, when applied to forming a wound care dressing, the collagen is processed: to control its mechanical properties in such as way than more than 80% of the collagen remains after pronase treatment; to result in a controlled hemostatic response without the generation of excessive intractable clotting; and to provide biological signals to the wound bed to capitalize on the regenerative capabilities of the native tissue. Upon wound administration of the wound care dressing made in accordance with the present invention, hemostasis is achieved within 120 seconds. Upon wound administration of the wound care dressing made in accordance with the present invention, immediate wicking of bodily fluids and even redistribution throughout the matrix. Further the wound care dressing manufactured according to the above process maintains its physical integrity and structural characteristics even after saturation with bodily fluids, and is entirely biodegradable and bioresorbable. This wound care dressing provides ease of wound excavation without toxic residuals or risk of re-injury. The collagen wound dressing is designed to work in concert with a topical, breathable, and analgesic hydrogel component and the hydrogel component can be loaded with a variety of therapeutic pharmaceutical agents, biologics and other active ingredients. The hydrogel/collagen bimodal wound dressing system can be used with Negative Pressure Wound Therapy and Cellular therapies.

Figure 3A:
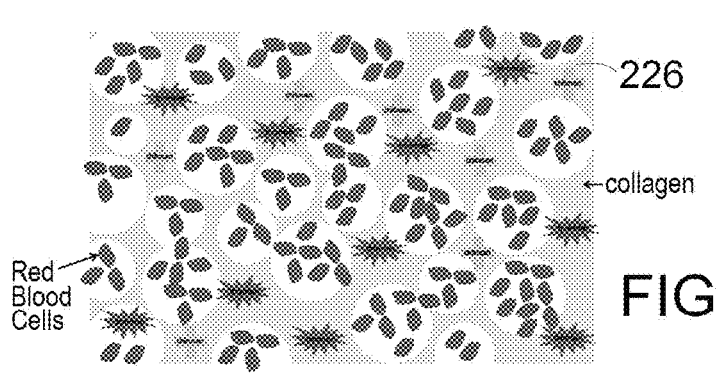
FIG. 3A is a schematic illustration of the collagen formed according to the present invention to illustrate the hemostat features of a wound dressing formed according to the present invention.

The wound care dressing made in accordance with the present invention forms an improved hemostatic dressing for non-compressible wounds, i.e. wounds where pressure cannot be directly applied, therefore the dressing needs to stop the bleeding without any manual pressure application. The hemostat features of the present invention are described in connection with schematic FIG. 3A, namely i) a biological mechanism in which Thrombin and collagen will act as procoagulants to initiate spontaneous clotting, ii) an adherent mechanism in which chitosan will provide intimate wound coverage by adhering to the tissue and the hemorrhaging vessel due to its inherent positive charge, and it is also noteworthy that chitosan is also a bactericidal agent, and iii) and Aggregate mechanism wherein the nano-porous architecture of the sponge or scaffold 228 will facilitate the immediate absorption of red blood cells and platelets and there uniform distribution within the pores of the scaffold 228 which will result in an interconnected network of cellular aggregates that enhances hemostasis and enables the formation of an effective uniform blood plug.

Figure 3B:
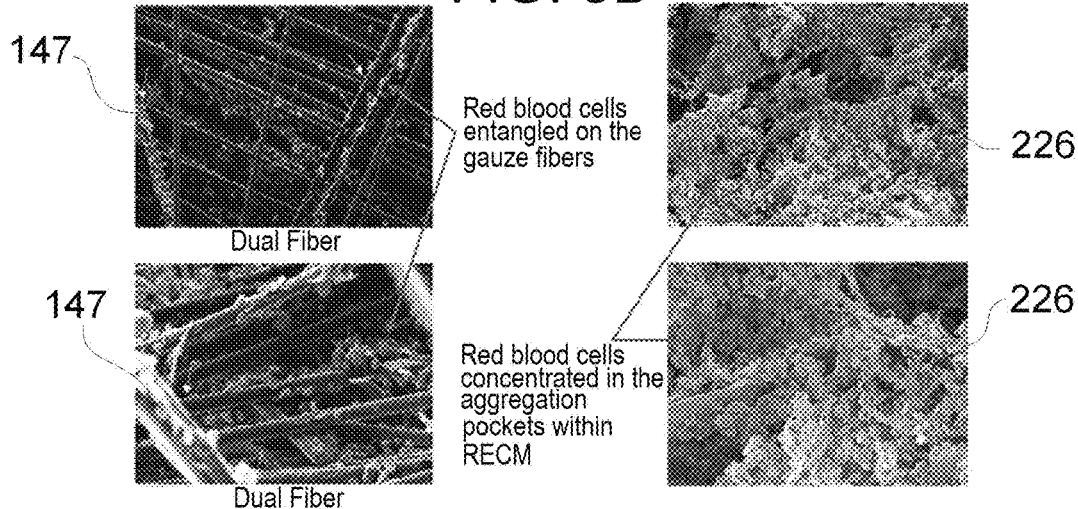
FIG. 3B are two SEM images demonstrating the hemostatic function of gauze compared side by side with two SEM images demonstrating the hemostatic function of the scaffold of the present invention.
Figure 3C:
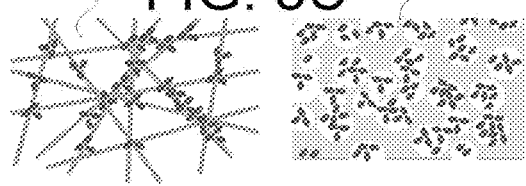
FIG. 3C is a schematic image demonstrating the hemostatic function of gauze compared side by side with a schematic image demonstrating the hemostatic function of the scaffold of the present invention.

The aggregation pockets in the wound care dressing, called RECM by applicant, formed by the matrix or scaffold 226 of the present invention serve a hemostatic function where concentration of platelets and red blood cells is dramatically increased (compared to gauze 147, for example) to enhance hemostatic as evident in the FIG. 3B. This is also schematically illustrated in the comparative schematic FIG. 3C which also illustrates this hemostatic function of the scaffold 226 relative to gauze 147:

The collagen wound care dressing made in accordance with the present invention represents a better material selection than cellulose dressings as cellulose is inflammatory and is not the natural scaffolding protein of the human body which is collagen. The shape of the wound care dressing of the invention can be any convenient shape, however discs or rolls may offer ease in application.

The applicants have tested the wound care dressing formed by the collagen matrix of the present invention in a preliminary animal study. Hanford cross female pigs (~25 kg) were anesthetized using Telazol (500 mg IM for pre-anesthesia, Isoflourane 1-3% inhalant anesthesia-delivered by oxygen). The pigs were positioned lying on their ventral end, with their dorsal (back) skin exposed. Full thickness wounds were surgically introduced in the dorsal skin tissue. The matrix of the present invention and a control were applied to respective wounds and their performance was documented in vivo. Spleen wounds were introduced using a 4 mm biopsy punch and the dressings were placed on top of the wound to evaluate their hemostatic and blood distribution properties. The matrix of the present invention was found to immediately absorb blood and achieve hemostasis, and to distribute blood uniformly throughout its matrix and achieve hemostasis, and to maintain structural integrity even when fully saturated with blood.

The wound care dressing made in accordance with the present invention, a reinforced 100% collagen matrix, has architectural elasticity, i.e the architecture of the matrix is restored after the load is removed. In other words it acts as a spring-loaded matrix. This collagen matrix wound care dressing is perfect for non-compressible wounds because it can be placed in the wound cavity and then spontaneously expand pushing against the wound bed without any manual pressure application. A very important feature is that collagen matrix maintains its architecture even after being completely saturated with blood. The advantage of the present matrix as a wound care dressing is it can be placed as a compressed collagen dressing in a wound and released so it will automatically "pop-open" or expand to fill the wound cavity without leaving any dead space.

Without intending to be bound by theory, it is believed that the "Syneresis" and "Water potential" can account for some of the improved mechanical properties exhibited by the matrix of the present invention. Syneresisis the extraction or expulsion of a liquid from a gel, as when lymph drains from a contracting clot of blood. Syneresis can also be observed when the amount of diluent in a swollen polymer exceeds the solubility limit as the temperature changes. Water potential is the potential energy of water per unit volume relative to pure water in reference conditions. Water potential quantifies the tendency of water to move from one area to another due to osmosis, gravity, mechanical pressure, or effects such as surface tension. These two mechanisms help define the difference between similer prior structures in wound care and the present invention with respect to the "spring loading" or "architectural elasticity".

The preferred collagen matrix of the present invention can be defined by the following three tests: i) Pronase degradation test: wherein more than 65% of the matrix weight remains after pronase treatment; ii) Differential Scanning calorimetery (DSC): The glass transition of the matrix will be higher than 37 C; and iii) Compression testing: the architectural elasticity of the matrix is defined as the return to at least 60% of the original dimensions of the matrix in dry and/or wet state within 30 seconds after the application of a compressive force.

Within the mold it is possible to include a polymeric sheet, and the crosslinked collagen may be introduced into the mold so as to encapsulate the sheet prior to drying. In such embodiments, the polymeric sheet may be bare or may be surface treated with one or more biomolecules such as heparin or with a hydrogel. The sheet may be solid or perforated, and may be a woven or non-woven mesh. Polyolefin mesh is particularly suitable, namely polypropylene mesh and polyethylene mesh. These polyolefin meshes are well known as surgical hernia repair fabrics. In certain application it may be desirable to include the mesh on one surface of the device with the cross linked collagen on the other side, wherein the mold can include projections within the mesh to maintain the mesh openings as open as may be desired. In certain application it may be desirable to include the mesh fully encapsulated within the collagen scaffold using typical insert molding techniques, e.g. the mold can include small pins supporting the mesh till the collagen can support the mesh, or the mesh can be suspended within the mold till the collagen can support the mesh. It may be desirable to reinforce the collagen with a biodegradable or bio-absorbable polymer such as Polylacticglycolic acid (PLGA), polyglycolic acid, polylactic acid, polydioxanone, and caprolactone or Electrospun collagen fiber. Further it may be desirable to bond the collagen to the supporting substrate such as through a covalently bonding to assure the final structure maintains integrity.

In an alternative embodiment, a composite article may be formed in accordance with the invention, wherein a polymeric sheet such as a polyolefin mesh is surface treated with a hydrogel such as via plasma deposition, and immediately prior to, simultaneously with, or immediately after step (b), at least a portion of reactive functional groups on the collagen may be reacted with one or more functional groups on the hydrogel. In a particular embodiment, the hydrogel comprises poly(2-acrylamide-2-methylpropanesulfonic acid; PAMPS). Additional biomolecules such as growth factors, GAGs, antibiotics, heparin and the like may be covalently bonded to or impregnated into the hydrogel.

The drying step of the process yields a porous, crosslinked collagen article that demonstrates a pore size of 10 to 500 microns, such as 20 to 125 microns, or 20 to 250 microns. The crosslinked collagen article demonstrates a tensile strength of at least 0.15 N/mm$^2$, such as at least 0.5 N/mm$^2$ or at least 1.0 N/mm$^2$. In specific embodiments, the crosslinked collagen article is capable of holding a suture without failure.

The method of the present invention is useful in the preparation of various medical scaffolds such as hernia repair or prevention prosthetics, wound care dressings, and surgical incision closure members. The crosslinked collagen articles prepared according to the method of the present invention demonstrate hemostatic properties, and are capable of achieving hemostasis (stoppage of bleeding) in less than sixty seconds; hemostasis in 30 seconds has been demonstrated. Moreover, the crosslinked collagen articles of the present invention perform hemostasis and fluid absorption homogeneously throughout the collagen matrix, without deformation, thereby minimizing trauma to surrounding tissue when used as a medical scaffold, in particular, as a wound dressing.

FIG. 5a is an SEM image of a sample of fibrous collagen 226 that has undergone the crosslinking process of the present invention, prepared for use as a wound dressing. It is directly comparable to FIG. 4a, which is an SEM image of a sample of conventional fibrous collagen that has not undergone the process of the present invention.

FIG. 5b is an SEM image of the sample of fibrous collagen 226 from FIG. 5a, after administration to a wound as a dressing. It is directly comparable to FIG. 4b, which is an SEM image of the sample of fibrous collagen from FIG. 4a, after administration to a wound as a dressing. The crosslinked dressing shown in FIG. 5b is saturated with red blood cells, whereas the non-crosslinked sample shown in FIG. 4b has only a few red blood cells distributed within.

FIG. 6 is a graphical comparison of the blood absorption per gram of wound dressing per second of various wound dressings. "C" represents PURACOL PLUS®, a commercially available collagen wound dressing available from Medline Industries, Inc. "SF" and "XSF" represent a non-crosslinked, insoluble fibrous collagen and its analogous crosslinked form prepared in accordance with the present invention, respectively. "XHSF" represents a heparinized version of "XSF". "P76" and "XP76" represent a non-crosslinked, fibrous bovine collagen and its analogous crosslinked form prepared in accordance with the present invention, respectively.

FIG. 6 demonstrates that the average blood absorption rate of each of the crosslinked collagen samples is consistently higher than that of the analogous non-crosslinked counterparts, and that the average blood absorption rate of each of the crosslinked collagen samples is consistently higher than that of the commercially available control.

The degradation rate of a wound dressing ideally matches the regeneration rate of the injured tissue. Optimally, the wound dressing resists degradation for thirty days to provide enough time for cells in surrounding tissue to colonize the wound dressing and initiate tissue regeneration. Crosslinked collagen articles of the present invention demonstrate a collagenase degradation of less than 10 percent by weight after thirty days and a pronase degradation of less than 10 percent by weight after thirty days.

The crosslink density of the collagen articles of the present invention improves the mechanical and chemical stability of the collagen and provides the desired prolonged functional performance of the collagen articles.

In a PRONASE DEGRADATION TEST used to determine resistance of crosslinked collagen articles prepared in accordance with the present invention to degradation by pronase, 200 mg of pronase is dissolved in 35 ml of Tris HCl buffer of pH 7.4. The pronase solution is heated to 37° C. in an incubator for 60 minutes under agitation. Five ml of pronase solution is added to a 0.015 g collagen sample and returned to the incubator under agitation. Observations are taken at regular intervals.

Crosslinked collagen articles prepared in accordance with the present invention are resistant to pronase degradation when subjected to the PRONASE DEGRADATION TEST described above for at least five hours, and have demonstrated high resistance to pronase degradation when subjected to the PRONASE DEGRADATION TEST described above for at least 24 hours. High Resistance to pronase degradation is defined as less than 10 percent degradation of the collagen by weight.

In FIG. 7, a two collagen molecules 11 crosslinked with each other are depicted. Each collagen molecule 12 is a triple helix. There are intrahelical crosslinks 13 and interhelical crosslinks 14 shown.

FIG. 8 is an illustration of a medical device comprising a crosslinked collagen molecule surface treated with a hydrogel and containing biomolecules and illustrates a medical device 21 comprising a composite article prepared according to the process of the present invention. The composite article comprises a crosslinked collagen matrix 22 surface treated with hydrogel 25. A biomolecule 23 such as gentamicin sulfate (GS) may be impregnated or reacted into the hydrogel for microbial action. Additional collagen molecules may be chemically bonded to the hydrogel, forming a top layer that encourages cellular infiltration when used within the body.

FIG. 9 illustrates a medical device 31 comprising a composite article prepared according to the process of the present invention. The composite article comprises a crosslinked collagen matrix 32 with a biomolecule 34 such as heparin reacted onto the crosslinked collagen matrix 32 via covalent bonds 33, forming a layer that encourages optimum anti-inflammatory response when used within the body.

A further enhancement of the present invention is "double enhanced crosslinking". With the above description this new aspect can be easily described as crosslinking the collagen by activating two different sets of functional groups on the collagen: first and Epoxy crosslinking at pH 3+/−3 and second Carbodiimide/NHS at pH 6+/−3.

A reinforced collagen matrix formed according to the present invention provides: Architectural elasticity/spring-loaded-ness; Controlled biodegradability {if the collagen degrades very quickly then the cells will not have enough time to generate their own collagen (extracellular matrix) and healing is compromised which usually leads to fibrosis (scarring) which is the body's way to just fill up the wound gap with fibrotic tissue. (pronase testing)}; Cellular tensegrity (Tensegrity is the term used to defined the ability of the cells to communicate via mechanically transduced signals) In a crosslinked collagen matrix, every cellular movement or attachment is sensed by the surrounding cells which allows them to coordinate their functions as a single functional unit. This can be verified by staining the cytoskeleton of cells; and Improved strength and mechanical properties verified by DSC (differential scanning calorimetry) and tensile testing.

A further enhancement of the present invention is the introduction of channels with certain sizes into the collagen matrix formed according to the present invention, particularly for wound care applications. Preferably channels 10 um to 1000 um in size and configures to influence cell mobility and differentiation into the dressing. The additional d the channels allows for manipulation of the density and specific configuration of the channels to modulate the mechanical properties of the wound care dressing. The textured channels may be formed with molds and may be configured to improve cytocompatibility in the wound dressing.

The preferred embodiments described above are illustrative of the present invention and not restrictive hereof. It will be obvious that various changes may be made to the present invention without departing from the spirit and scope of the invention. The precise scope of the present invention is defined by the appended claims and equivalents thereto.

What is claimed is:

1. A method of preparing a crosslinked, collagen-based wound care dressing, comprising:
   (a) immersing a sample of fibrous and/or non-fibrous collagen in a buffered acidic, aqueous solution comprising an alcohol, wherein the immersion of the sample of fibrous and/or non-fibrous collagen is conducted prior to crosslinking of the collagen;
   (b) subsequent to step (a), contacting the collagen in a separate solution with a catalytic component comprising 1-ethyl-3-[3-dimethylaminopropyl] carbodiimide hydrochloride (EDCl) for a time at least sufficient to effect reaction between amino and carboxyl groups present on the collagen and to yield crosslinked collagen, wherein the crosslinked collagen is resistant to pronase degradation when subjected to a pronase degradation test for at least five hours; and
   (c) drying the crosslinked collagen to yield a porous, crosslinked collagen article, wherein the pores of the porous, crosslinked collagen article have a pore size of 10-500 microns.

2. The method of claim 1, wherein the collagen is a mixture of fibrous and non-fibrous collagen.

3. The method of claim 1, wherein the collagen is obtained from human tissue.

4. The method of claim 1, wherein the collagen comprises an extracellular matrix.

5. The method of claim 1, wherein the acidic, aqueous solution comprises a mixture of a $C_1$ to $C_6$ alcohol and a non-carboxylic acid buffer.

6. The method of claim 5, wherein the acidic, aqueous solution comprises a mixture of ethanol and 2-morpholinoethane sulfonic acid (MES).

7. The method of claim 1, wherein in step (b), the catalytic component further comprises N-hydroxysulfosuccinimide (NHS).

8. The method of claim 1, wherein in step (b), the collagen is contacted in solution with the catalytic component for a time at least sufficient to effect reaction between amino and carboxyl groups present on the collagen and to yield crosslinked collagen that is resistant to pronase degradation when subjected to the pronase degradation test for at least 24 hours.

9. The method of claim 1, wherein in step (b), the collagen is contacted with the catalytic component for at least one hour.

10. The method of claim 1, wherein prior to step (b), at least a portion of reactive functional groups on the collagen are reacted with one or more $C_2$ to $C_{18}$ carboxylic acids having amino and/or hydroxyl functional groups.

11. The method of claim 1, wherein prior to step (b), a portion of amino functional groups on the collagen are reacted with an aldehyde.

12. The method of claim 1, wherein immediately prior to, simultaneously with, or immediately after step (b), at least a portion of reactive functional groups on the collagen are reacted with one or more biomolecules separate from the collagen having carboxylic acid, amino and/or hydroxyl functional groups thereby surface treating the collagen.

13. The method of claim 12, wherein the biomolecule is selected from one or more of a fibroblast growth factor, a vascular endothelial growth factor, a glycosaminoglycan (GAG), an antibacterial agent, an antimicrobial agent, an anticoagulant, an antithrombotic agent, a platelet agent, an anti-inflammatory compound, an enzyme, a bioreaction catalyst, a hormone, a drug, a vitamin, an antibody, an antigen, a nucleic acid, a dye, a DNA segment, an RNA segment, a protein, and a peptide.

14. The method of claim 13, wherein the biomolecule comprises heparin.

15. The method of claim 1, wherein the crosslinked collagen article demonstrates a tensile strength at ambient temperature such that it is capable of holding a suture without failure.

16. The method of claim 1, wherein the crosslinked collagen article demonstrates a tensile strength at ambient temperature of at least 0.15 $N/mm_2$.

17. The method of claim 1, wherein in step (c), the crosslinked collagen is freeze dried.

18. The method of claim 1 wherein after step (b) and prior to step (c) the crosslinked collagen is introduced into a mold.

19. The method of claim 18, wherein a polymeric sheet is present inside the mold and the crosslinked collagen is introduced into the mold so as to encapsulate the sheet.

20. A method preparing a crosslinked, collagen-based wound care dressing, comprising:
   (a) immersing a sample of fibrous and/or non-fibrous collagen in a buffered acidic, aqueous solution comprising an alcohol, wherein the immersion of the sample of fibrous and/or non-fibrous collagen is conducted prior to crosslinking of the collagen;

(b) subsequent to step (a), contacting the collagen in a separate solution with a catalytic component comprising 1-ethyl-3-[3-dimethylaminopropyl] carbodiimide hydrochloride (EDCl) for a time at least sufficient to effect reaction between amino and carboxyl groups present on the collagen and to yield crosslinked collagen, wherein the crosslinked collagen is resistant to pronase degradation when subjected to a pronase degradation test for at least five hours; and (c) drying the crosslinked collagen to yield a porous, crosslinked collagen article, wherein the pores of the porous, crosslinked collagen article have a pore size of 10-500 microns wherein after step (b) and prior to step (c) the crosslinked collagen is introduced into a mold, and further including the introduction of channels 10 um to 1000 um in size into the cross linked collagen via the mold.

* * * * *